United States Patent [19]

Zappia et al.

[11] Patent Number: 5,073,546
[45] Date of Patent: Dec. 17, 1991

[54] LIPOPHILIC SALTS OF S-ADENOSYL-L-METHIONINE (SAM) WITH ACYLATED TAURINE DERIVATIVES

[76] Inventors: Vincenzo Zappia, Via S. Giacomo Dei Capri 109/B; Mario DeRosa, Via E. Nicolardi, 188, both of 80100 Napoli, Italy

[21] Appl. No.: 469,583

[22] Filed: May 29, 1990

[51] Int. Cl.$^5$ ............ A61K 31/70; C07H 19/167
[52] U.S. Cl. .......................... 514/46; 514/45; 536/24; 536/26
[58] Field of Search ............ 536/24, 26; 514/45, 514/46

[56] References Cited

U.S. PATENT DOCUMENTS

| | | | |
|---|---|---|---|
| 3,893,999 | 7/1975 | Fiecchi | 536/26 |
| 3,954,726 | 5/1976 | Fiecchi | 536/26 |
| 4,057,686 | 11/1977 | Fiecchi | 536/26 |
| 4,465,672 | 8/1984 | Gennari | 514/46 |

FOREIGN PATENT DOCUMENTS 0162324 11/1985 European Pat. Off. .............. 536/26
0191133 8/1986 European Pat. Off. .............. 536/26

*Primary Examiner*—Johnnie R. Brown
*Assistant Examiner*—Anita Varma
*Attorney, Agent, or Firm*—Walter H. Schneider

[57] ABSTRACT

Liposoluble salts of S-adenosyl-L-methionine (SAM) with acyl derivatives of taurine having the formula:

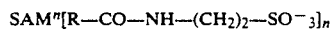

$$SAM^n[R-CO-NH-(CH_2)_2-SO^-_3]_n$$

in which R—CO is a member selected from $C_{12}-C_{26}$ saturated and unsaturated, linear and branched acyl, and $C_2-C_{26}$ cycloalkyl-substituted acyl, and n is from 3 to 6 according to the SAM charge, and pharmaceutical compositions containing the salts.

2 Claims, No Drawings

LIPOPHILIC SALTS OF S-ADENOSYL-L-METHIONINE (SAM) WITH ACYLATED TAURINE DERIVATIVES

This invention relates to stable salts of the S-adenosyl-L-methionine (SAM) with taurine acyl derivatives, to processes for obtaining them, and to therapeutic formulations containing said novel salts as their active constituents.

The SAM S-adenosyl-methionine, currently known as SAM and ubiquitarily occurring in living organisms, performs a number of important biochemical functions: (a) it acts as a methyl group donor in a large number of transmethylation reactions; (b) it is a substrate of a specific lyase that converts the molecule to methylthioadenosine (MTA) and homoserine; (c) it functions as an aminobutyric chain donor to tRNA; (d) it is an aminoacidic chain donor in the biosynthesis of biotin; (e) it is a donor of the adenosyl moiety; (f) it is a promoter of lysin-1,3-amino mutase, threonine synthetase, pyruvate formate lyase, and N5-methyltetrahydrofolate-homocysteine methyltransferase; (g) it is an inhibitor of H ribonuclease, methylene tetrahydrofolic reductase, and ethanolaminephosphate cytidyltransferase; (h) it is required for the bacterial and leukocyte chemotaxis; (i) it is required in the prokaryote and eukaryote restriction and modification system of the DNA. Moreover, the decarboxylate product thereof, the S-adenosyl-(5')-3-methylthiopropylamine (deca-SAM) acts as a propylamine group donor in the biosynthesis reactions of polyamines. There exists a recent exhaustive literature dealing with these multiple biological roles of SAM and deca-SAM (Zappia V. et al., "Biomedical and Pharmacological roles of Adenosylmethionine and the Central Nervous System", page 1, Zappia V. Et al., Eds., Pergamon Press N.Y., 1979; Paik W. K. et al., "Protein Methylation", Maister A. Ed., J. Wiley & Sons N.Y., 1980; "Biochemistry of S-Adenosylmethionine and Related Compounds", Usdin E. et al. Eds., Mac Millan Press L.t.D., 1982). As a consequence of these complex biochemical roles, the SAM exerts a series of effects summarized in the following table.

The SAM is obtained from yeasts grown on media containing cysteine (Cantoni G. L., "Methods in Enzymology", 3, 600 1967).

The present production of SAM is thereby carried out by fermentation using Saccharomyces cerevisiae. The SAM production, in the experimentations according to the present invention, has been carried out by means of a new hyperproducing microorganism Saccharomyces sake Kyokai n. 6 (Yamada, M. et al. in "Third European Congress on Biotechnology", Vol. 1, Verlag Chemie, Weinheim), allowing yields up to 9 g of SAM per liter of culture medium.

The main problem for the large-scale use of SAM as a drug, is the thermal instability of the molecule. Infact, 5'-[[(3S)-3-amino-3-carboxy-propyl]methyl-(S)-sulfonio-5'-deoxyadenosine, which is the biologically active form, is easily degraded particularly as a consequence of an intramolecular nucleophilic attack of the carboxylic carbon on the aminoacidic $\gamma$ methylene which is highly activated by the nearly sulfonium group (Zappia V. et al. in "Transmethylation", Usdin E. et al. Fds. Elsevier N.Y., 1979; Zappia V. et al. in "Methods in Enzymology", 94, 73, 1983). This process is remarkably reduced at very low pH values, preventing the ionization of the aminoacidic carboxy group. The state of charge of SAM is a function of pH because of the presence of more ionizable sites.

At acidic pH, SAM behaves as a multiple charge cation and its salts, as crystalline solids, have a thermal stability critically connected with the characteristics of the anion. Also in this case, as well as in solution, SAM is mainly degraded to methylthioadenosine (MTA) and homocysteine.

Particularly stable salts have been recently described (U.S. Pat. No. 4,057,686). Similar salts, which may be orally administered, are disclosed in EP-A-0162324.

SAM salts are normally hydrosoluble, in some case according to the pH and their bioavailability after oral administration is not usually very high. It has now been found that SAM salts with lipophilic acyltaurines of formula $$SAM^{n+}[R-CO-NH-(CH_2)_2-SO^-_3]_n \qquad I$$

TABLE 1

| | Pharmacologic Effects of S-Adenosylmethionine | |
|---|---|---|
| EFFECTS | TEST MODEL | USE IN CLINICAL PATHOLOGY |
| ANTI-INFLAMMATORY | ACUTE EDEMA FROM CARRAGEENIN AND WHITE OF EGG CHRONIC EDEMA IN ARTHRITIS FROM ADJUVANTS | OSTEOARTHRITIS (improves muscular spasms, etc.) |
| ANALGESIC | PAIN FROM MYOTASIS (stretching of a muscle) | OSTEOARTHRITIS |
| HEPATOPROTECTIVE | STEATOSIS FROM HYPERLIPIDIC AND HYPERPROTEINIC DIET STEATOSIS FROM ACUTE INTOXICATION CAUSED BY ALCOHOL OR HEPATOTOXIC AGENTS (CARBON TETRA-CHLORIDE, BROMOBENZENE) | ACUTE AND CHRONIC DISEASES OF THE LIVER |
| BILE FLUIDIFYING | INTRAHEPATIC OR ESTROGEN-INDUCED BILE SUPER-SATURATION CHOLESTASIS | GRAVIDIC CHOLESTASIS CHOLESTASIS CAUSED BY TREATMENT WITH ESTROGENS |
| ENHANCING OR STRENGTHENING (THE ACTION OF LEVODOPA) | — | PARKINSON'S DISEASE (IMPROVES AKINESIA AND RIGIDIDY) |
| SLEEP INDUCING | — | DISORDER OF SLEEP MECHANISM OR OF WAKING-SLEEPING RHYTHM |
| ANTIDEPRESSANT | — | REDUCES OR RESOLVES SYMPTOMATOLOGY IMPROVES THE PSYCHOAFFECTIVE SPHERE IN ATHEROSCLEROSIS | where R—CO is a $C_{12}$–$C_{26}$, saturated or unsaturated, linear or branched or cycloalkyl - substituted acyl and n is from 3 to 6 according to the SAM charge, are endowed with advantageous properties, so as to make them particularly useful for the preparation of pharmaceutical or cosmetic compositions.

The state of charge of SAM at a pH up to 2.5 allows infact an effective lipophilic cation-anion interaction, giving a poorly dissociated salt, which precipitates from the solution yielding a white solid.

At higher pH up to 5, gelly systems are obtained, whose consistency is function of the concentration of the formed SAM salt. At pH higher than 5 the state of charge of SAM allows an interaction cation - lipophilic anion, characterized by stoichiometry higher than 0.5. These salts are poorly hydrophobic and they are therefore sufficiently hydrosoluble. The stoichiometry of the SAM salts is not only dependent on the pH of the medium, but also on the hydrophobicity degree of the used acyl-taurine. For the salt stability and precipitation yield the stoichiometry 1:4–5 (SAM moles: lipophilic anion salt) is particularly preferred and may be obtained in the pH range of 1–1.5, with $C_{12}$–$C_{26}$ acyl-taurines.

SAM salts of formula I are waxy, white solids, not hydrogroscopic and stable at room temperature, so as to allow the pharmacological or cosmetical use.

They are insoluble in water and soluble in organic solvents.

It is also convenient the preparation of lipophilic salts I solutions in lipidic phases, particularly lecithins, by evaporation of chloroform solutions containing the two species. Micellar and/or liposomial solutions, characterized by a chemical stability of SAM in solution higher than that of other salts at the same pH, may be easily obtained by sonication in water of the salts I. Said solutions, subjected to lyophilization or spray-drying, give a solid phase which is easily dispersed by water addition forming a stable micellar and/or liposomial solution. This behaviour is particularly interesting for the development of injectable and oral formulations providing a rapid absorption of the active principle.

The precipitation of SAM is preferably carried out at pH 1–1.5 in high yields, even from very diluted solutions ($<1$ μm) of the sulfonium compound. The precipitation yields at optimal pH values and SAM concentration ($\simeq30$ mM) are higher than 90% and the separation of the two phases is complete at room temperature in a few minutes. The precipitation usually occurs by adding to a stirred SAM solution at adjusted pH a 5-6 times molar excess of a concentrated acyltaurine aqueous solution. The process is absolutely not critical and an inverted procedure (SAM addition to the acyltaurine solution) does not change yields and stoichiometry of the precipitated salt. The obtained salt is usually recovered by decantation or by centrifugation or filtration. It is usually washed with water and dried at temperatures not higher than 50° C. Alternatively, the salts, after washing with water, are dissolved in chloroform/acetone (1:1 v/v), evaporating the solvent and the residual water as an azeotrope under vacuum. Alternatively, the salt may be precipitated from the organic solution by addition of acetone up to a $CHCl_3$/acetone ratio of 1:2 (v/v). The precipitate is then recovered as usual.

The SAM precipitation from acidic aqueous solution is not hindered by the presence of even high concentrations of neutral or ionic molecules and it is highly specific since the lipophilic SAM salts may be selectively precipitated in the presence of MTA, main degradation product of the sulfonium compound. This allows the preparation of SAM salts I directly from SAM enriched yeast extracts.

The acyltaurines may be conveniently prepared by reacting taurine with a slight stoichiometric excess of an activated form of the carboxylic acid (chloride, anhydride, imidazolide etc.) in the presence of dimethylaminopyridine as a catalyst. The reaction may be carried out in heterogeneous phase in organic solvents or in the absence of solvents when the acylating reagent is liquid and is complete in a few hours at 80° C. After evaporation of the solvent and washing of the residue with petroleum ether, the acyl derivative is solubilized in water where it forms supermolecular aggregates of micellar and/or liposomial kind, and it is subjected to diafiltration on membranes having cut-off 10,000, to remove low-molecular weight hydrosoluble contaminants. The so obtained solution may be directly used for the SAM precipitation.

The salts I are characterized by a remarkable bioavailability. The plasmatic concentration in the rat after administration by different routes of (Met-$^{14}$C) SAM-oleyltaurine and (Met-$^{14}$C) SAM-mirystoyltaurine are remarkably higher than that obtained after administration of (Met-$^{14}$C) SAM-sulfate or (Met-$^{14}$C) SAM-sulfate-paratoluensulfonate.

In comparison with the previously known SAM salts with non-natural sulfonic acids, the acyltaurine SAM salts provide a remarkable improvement. In fact, the acyltaurines, because of their natural origin, are characterized by high bioavailability and by the lack of contra-indications, even when administered at higher dosage than taht corresponding to 1 g/die of SAM.

Thus, while the non-natural sulfonic anions previously used for some of the SAM stabilization forms cannot generally by metabolized and cause undesired side-effects, the acyltaurines are degraded by amidases usually present in the organism yielding taurine and fatty acid, which are usual cellular component which are daily ingested with food in by far higher doses.

The lipophilic salts of formula I exhibit, in comparison with the other known salts, important advantages, namely:
a) chemical stability;
b) liposolubility;
c) ability to give stable liposomial and/or micellar suspension;
d) higher bioavailability;
e) lower toxicity;
f) they allow the preparation of pharmaceutical forms other than the oral and injectable forms, up to now used, such as rectal or topical forms;
g) the used lipophilic anion is biocompatible and its bio-degradation releases molecular components normally present in the organism.

The invention refers therefore also to pharmaceutical or cosmetic compositions containing as the active principle one of the lipophilic salts of SAM of formula I in admixture with the usual carriers.

The pharmaceutical compositions of the invention may be used in all the therapeutic indication already known for SAM and they are particularly useful in pathologies correlated with aging processes.

The cosmetic compositions of the invention are particularly useful in the prevention and treatment of the aging processes of the skin and, more generally, as components of formulations effective in the cellular regeneration.

Examples of pharmaceutical compositions according to the invention are those suited for oral, injectable, rectal or topical use, such as capsules, tablets, suppositories, vials, creams etc.

Examples of cosmetic compositions of the invention are provided by creams, pastes, lotions, emulsions, milks, oils and the like.

The daily doses and the administration modes depend on several factors (intended use, patient's conditions) but they will in any way be easily determined, on a case by case basis, in a not critical way also as a consequence of the very low toxicity of the components.

The compositions of the invention may comprise other therapeutically or cosmetically effective agents endowed with complementary activity.

The following examples illustrate the invention without limiting the scope thereof.

EXAMPLE 1

9 kg of *Saccaromyces sake* kyokai n. 6, grown on methionine rich culture medium, according to (Shiozaki S. et al. (Agric. Biol. Chem., 48, 2293, 1984) are lysed by treatment of the cellular paste with 1.5 liters of ethyl acetate and adding thereafter 24 l of $H_2SO_4$ 0.5 N after 30 minutes. After filtration and washing, 60 liters of extract containing 0.4 kg of SAM are obtained, whose pH is adjusted to 4.5 by NaOH. The SAM is purified using a 6 l ion-exchange 100-200 mesh Bio-Rex 70®column. After charging, the column is washed with 10 l of distilled water and 50 l of $H_2SO_4 10^{-2}N$, SAM is then eluted with 10 l. of $H_2SO_4$ 0.5N, having, in the collected eluate, a titer of 13 g/l. The pH of this solution is brought to 1 with NaOH and then oleyl taurine is precipitated.

This is prepared by reacting at 70° C. for 10 hours 175 g of taurine, suspended in 1400 ml of anhydrous dimethylformamide (DMF), with 1148 g of oleic anhydride in the presence of 1 g of dimethylaminopyridine (DMAP) as a catalyst. After removal of the solvent under vacuum, the oily residue is repeatedly triturated with ethyl ether, 5,32 g of oleyl-taurine are obtained as a waxy, white solid. The 'H—NMR spectrum, recorded in $CDCl_3$, shows in the correct integration ratios the signals of the acyl moiety at δ 5.3; 2.4; 2.9; 1.6; 1.3; 0.9 and those of taurine at δ 3.7 and 4.7. 461 g of oleyl taurine dissolved in 2 l of $H_2O$ are then added to 7 l of the 3 mM SAM solution, pH 1, under stirring.

The immediate precipitation of a white precipitate, easily sedimenting, occurs. After centrifugation of the liquid phase, the precipitated is washed with water (1 l×2) and the lyophilized. 3.95 g of a waxy, white solid whose SAM: oleyl taurine stoichiometry is 1:4.2, are obtained.

EXAMPLE 2

16 l of a 3.3 mM SAM solution at pH 1.1 are precipitated with 102 g of oleyl taurine dissolved in 2 l of $H_2O$. A white solid precipitates, which is filtered. After washing with water and lyophilization, 87.9 g of salt having SAM: oleyl taurine ratio of 1:4.3 are obtained.

EXAMPLE 3

125 g of taurine, suspended in 500 ml of anhydrous pyridine, are reacted at 50° C. for 10 hours with 450 g of arachidonic acid chloride. After solvent evaporation under vacuum, the oily residue is first triturated in ethyl ether and then, after dissolution in water in form of a micellar and/or liposomial system, it is dialyzed against water to remove the low molecular weight contaminants.

The $^1H$—NMR spectrum, recorded in $CDCl_3$, shows in the correct integration ratio the signals of the acyl moiety at δ 5.3; 2.8; 2.4; 1.9; 1.6; 1.3; 0.9; and those of taurine at δ 33.7 and 4.6; 5.5 l of 3.3 mM SAM solution, pH 1, are precipitated under stirring at room temperature with 370 g of arachidonyl taurine, dissolved in 2 l of $H_2O$. The precipitate, recovered by filtration under pressure and washed twice with 0.51 of $H_2O$, is dissolved in 3 l of $CHCl_3$-acetone 1:1 (v/v). The organic solution is then evaporated under vacuum.

330 g of a waxy, white solid, having SAM: arachidonyl taurine stoichiometry 1:4.3, are obtained.

EXAMPLE 4

11 l of 33 mM SAM solution, pH 1, are precipitated with 740 g of arachidonyl taurine, as disclosed in Example 3, collecting the precipitate by centrifugation. After 2 washings with $H_2O$, the residue is first dissolved in 5 l of $CHCl_3$, precipitating thereafter the lipophilic salt by adding 10 l of acetone. The product collected by filtration is dried in inert gas flow. 580 g of a 1:4.5 SAM -arachidonyl taurine salt are obtained.

EXAMPLE 5

200 g of SAM - oleyl taurine salt of Example 1 are dissolved in 3 l of $CHCl_3$. 200 g of soy lecithin are added to this solution which is then evaporated. 400 g of soft paste wich may be considered a SAM salt solution in lecithin, are obtained. 50 g of this paste, sonicated in 1 l of $H_2O$, yield a micellar and/or liposomial solution stable in time.

We claim:
1. A lipophilic salt of S-adenosyl-L-methionine (SAM) of the formula

$$SAM^{n+}[R-CO-NH-(CH_2)_2-SO^-_3]_n$$

in which R-CO is a member selected from the group consisting of $C_{12}-C_{26}$ saturated and unsaturated, linear and branched acyl and $C_{12}-C_{26}$ cycloalkyl-substituted acyl, and n is an integer from 3 to 6 according to the SAM charge.

2. A composition comprising as the principal active ingredient an effective amount of a lipohilic salt of S-adenosyl-methionine according to claim 1 in admixture with an inert carrier.

* * * * *

UNITED STATES PATENT AND TRADEMARK OFFICE
CERTIFICATE OF CORRECTION

PATENT NO. : 5,073,546
DATED : Dec. 17, 1991
INVENTOR(S) : Vincenzo Zappia; Mario De Rosa It is certified that error appears in the above-identified patent and that said Letters Patent are hereby corrected as shown below:

On the Title page, the following should be inserted:

---[30] Foreign Application Priority Data

Oct. 9, 1987 [IT]    Italy-------------22213 A/87
Oct. 9, 1987 [IT]    Italy-------------22214 A/87---

Signed and Sealed this

Sixth Day of April, 1993

Attest:

STEPHEN G. KUNIN

Attesting Officer

Acting Commissioner of Patents and Trademarks